(12) United States Patent
Lee

(10) Patent No.: US 8,523,815 B2
(45) Date of Patent: Sep. 3, 2013

(54) SLIDING CORE FLUID DELIVERY DEVICE

(75) Inventor: Freddie Eng Hwee Lee, Singapore (SG)

(73) Assignee: B. Braun Melsungen AG, Melsungen (DE)

( * ) Notice: Subject to any disclaimer, the term of this patent is extended or adjusted under 35 U.S.C. 154(b) by 466 days.

(21) Appl. No.: 12/766,546

(22) Filed: Apr. 23, 2010

(65) Prior Publication Data
US 2012/0325320 A1 Dec. 27, 2012

Related U.S. Application Data

(60) Provisional application No. 61/173,717, filed on Apr. 29, 2009.

(51) Int. Cl.
*A61M 37/00* (2006.01)
(52) U.S. Cl.
USPC .......................... 604/131; 604/132
(58) Field of Classification Search
USPC ................ 604/131, 132
See application file for complete search history.

(56) References Cited

U.S. PATENT DOCUMENTS

| 5,105,983 | A | | 4/1992 | Sancoff et al. |
| 5,211,632 | A | * | 5/1993 | Tsukada ............... 604/132 |
| 6,024,724 | A | * | 2/2000 | Lee ..................... 604/132 |
| 7,618,432 | B2 | | 11/2009 | Pedersen et al. |

OTHER PUBLICATIONS

Office Action for U.S. Appl. No. 12/835,209 mailed Feb. 2, 2012.

* cited by examiner

*Primary Examiner* — Kevin C Sirmons
*Assistant Examiner* — Deanna K Hall
(74) *Attorney, Agent, or Firm* — RatnerPrestia

(57) ABSTRACT

A pump for the delivery of a fluid includes a core, a restrictor, and an expandable bladder. The core is configured to extend longitudinally along an axis of the pump. The restrictor is configured to limit the longitudinal extension of the core to a predetermined maximum length. The expandable bladder is attached to the support core in at least one position and configured to receive a fluid.

17 Claims, 3 Drawing Sheets

SLIDING CORE FLUID DELIVERY DEVICE

CROSS-REFERENCE TO RELATED APPLICATIONS

This application claims the benefit of U.S. Provisional Application No. 61/173,717 filed on Apr. 29, 2009, the content of which is hereby incorporated by reference in its entirety.

FIELD OF THE INVENTION

This invention relates to a fluid delivery device.

BACKGROUND

Elastomeric pumps are widely used in healthcare settings to deliver fluids and medication to patients. In some pumps, fluid is stored in a drug reservoir or bladder made of silicon or another rubber polymer. The bladder is attached to a fixed length central support core at positions along the core that are separated by a non-variable distance. When filled, the bladder expands and the increased surface area of the bladder stores energy that exerts pressure on the fluid, driving the fluid out of the bladder. The flow rate of the fluid is often limited by a restricting orifice such as a glass capillary or a section of PVC tubing.

Referring to FIG. 1, a typical flow profile 18 (i.e., flow rate vs. time) for a standard elastomeric pump shows that the flow rate of fluid from the pump is not constant during fluid delivery. Flow begins with a strong initial spike 20 in flow rate, continues with a trough-shaped phase 21 having a lower flow rate, and finishes with a slight second spike 22. While the troughs and peaks of such a profile may be averaged to provide a sufficient flow rate, in some cases, such as for the delivery of toxic medication or when a narrow therapeutic dose is required, the initial spike may result in an overdose or another undesirable situation.

The initial spike 20 is generated by the strong forces exerted on the fluid by the expanded bladder. To mitigate the initial spike in flow rate, a filled pump can be put aside for a waiting period before beginning fluid delivery in order to allow the bladder to lose some of its elasticity, thus reducing the forces exerted on the fluid therein.

The trough-shaped phase 21 results from a combination of two phenomena. As fluid exits the bladder, the bladder contracts and the energy stored in the bladder decreases. Thus, the pressure exerted by the bladder on the fluid decreases, causing the flow rate to drop. At the same time, however, the physical contraction of the bladder results in a thickening of the bladder walls, which causes the bladder to impose more pressure on the fluid. Initially, the first effect is prominent. As the bladder empties, the latter effect becomes progressively more prominent and manifests itself as the second spike 22 at the end of the fluid delivery.

If the thickness of the bladder walls is not uniform, the bladder will expand more rapidly in the thinner regions when receiving fluid, thus further accentuating the thickness variations. This effect causes the expanded bladder to have an asymmetrical shape, which in turn results in an uneven flow rate and variability in flow rate among like pumps. To combat this effect, the bladder is often enclosed in an outer cover that restricts its asymmetrical expansion, such as a rigid cover or a flexible and non-expandable cover. In some pumps, the bladder is formed of a rubber polymer that exerts force on the fluid therein and a silicone lining on the inside of the bladder that prevents the fluid from coming into contact with the rubber polymer.

SUMMARY

In a general aspect, a pump for the delivery of fluid includes a core configured to extend longitudinally along an axis of the pump, a restrictor configured to limit the longitudinal extension of the core to a predetermined maximum length, and an expandable bladder attached to the support core in at least one position and configured to receive a fluid.

Embodiments may include one or more of the following. The pump includes a cover enclosing the bladder and at least a portion of the support core. The cover has a size and shape such that when the bladder is filled with a fluid, the bladder has a size and position that are substantially independent of the size and shape of the cover. The cover is sized and dimensioned such that a gap exists between an outer surface of the bladder and an inner surface of the cover when the bladder is filled with fluid. The bladder is formed substantially of silicone. The position at which the bladder is attached to the core is selected based on at least one of a volume of the bladder when filled and a desired flow rate of a fluid delivered from the pump.

The core includes a first piece and a second piece configured to slide longitudinally relative to each other. The pump includes a connector for connecting the first piece and the second piece. The restrictor includes a ball bearing positioned in a channel. The length of the channel is determined based on the predetermined maximum length of the core. The support core is configured to expand longitudinally when fluid enters the bladder and to contract longitudinally when fluid exits the bladder. The pump is configured to deliver fluid at a substantially constant flow rate.

In another aspect, a method for the delivery of a fluid from a pump includes receiving fluid into a bladder and delivering fluid from the pump. Receiving fluid into a bladder includes extending a support core longitudinally along an axis of the pump and expanding the bladder. The extension of the support core is limited to a predetermined maximum length by a restrictor. Delivering fluid from the pump includes contracting the bladder and retracting the support core along the longitudinal axis of the pump.

Embodiments may include one or more of the following. Delivering fluid from the pump includes delivering fluid at a substantially constant flow rate. Extending the support core includes sliding a first piece of the support core longitudinally relative to a second piece of the support core. Expanding the bladder includes expanding the bladder to a shape and position that is substantially independent of a size and shape of a cover enclosing the bladder. The bladder is formed substantially of silicone.

A pump as described above has a number of advantages. In particular, the sliding core of the pump supplies an additional degree of movement to the pump as the bladder is filled or as fluid is delivered from the pump. This additional degree of movement affects the flow profile of the fluid delivery, enabling the pump to deliver fluid with a reduced initial spike or even no initial spike in flow rate. Furthermore, the sliding core allows the bladder to expand substantially symmetrically as it is being filled even if there are slight variations in the thickness of the bladder walls. The composition of the bladder as primarily silicone further facilitates the symmetric expansion of the bladder. As a result of this symmetric expansion, the bladder exerts a uniform pressure to the fluid inside, making possible a consistent flow rate during fluid delivery.

In this way, a relatively constant flow rate is maintained during a large portion of the delivery of fluid from the pump. The symmetric expansion of the bladder also helps to reduce or eliminate the spike in flow rate at the start of fluid delivery from the pump. A consistent flow rate is attainable as soon as the pump has been filled with fluid; no waiting period is necessary to relax the pressure exerted by the bladder on the fluid inside. Additionally, inter-device variability is reduced because the expansion of the bladder, and hence the pressure applied to the fluid contained therein, is consistent among like devices.

DETAILED DESCRIPTION

Figure 2A:
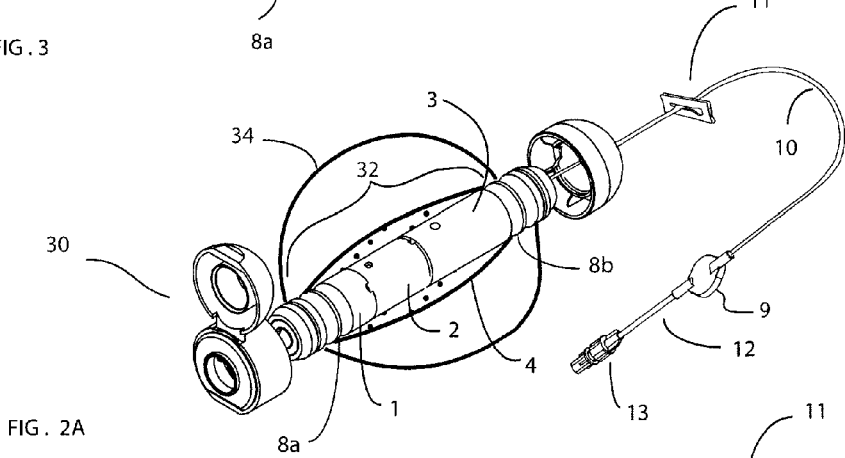
FIG. 2A shows a sliding core pump with a substantially empty bladder.

Referring to FIG. 2A, a sliding core pump 30 delivers fluids, such as antibiotics, pain relief drugs, chemotherapy agents, or other medications, to a patient. Pump 30 includes a generally cylindrical support core 32 carrying a bladder 4 and an outer cover 34. Fluid is stored within bladder 4, which exerts pressure on the fluid, forcing the fluid out of the pump through a fluid delivery line 10. A patient connector 13 (e.g., a Luer adapter) coupled to the end of fluid delivery line 10 facilitates the delivery of fluid to a patient. In some embodiments, fluid delivery line 10 is coupled to other components, such as an air trap and anti-microbial filter 9 or a micro-bore restrictor tubing 12, which can be, for instance, a glass capillary or a section of PVC tubing. A clamp 11 connected to fluid delivery line 10 starts and stops the flow of fluid from pump 30.

Figure 3:
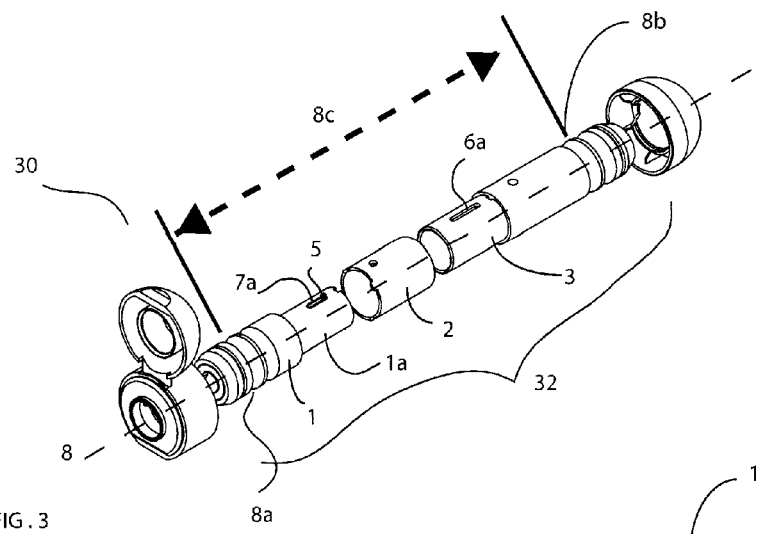
FIG. 3 is an expanded view of a portion of a sliding core pump.
Figure 2B:
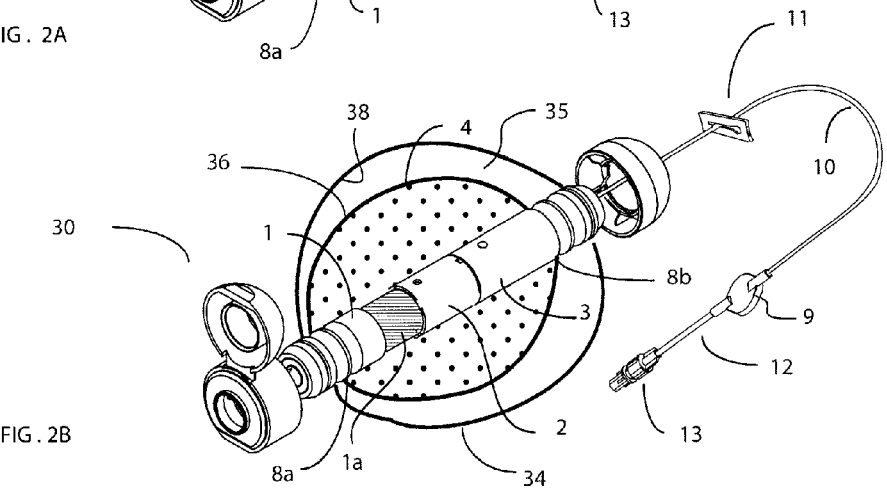
FIG. 2B shows a sliding core pump with a substantially full bladder.

Referring to FIGS. 2A and 3, support core 32 incorporates movable or telescopic components, including a first sliding core member 1 and a second sliding core member 3. Sliding core members 1 and 3 are held together with a collar-like connector 2. In another embodiment, first sliding core member 1 inserts into an annular cavity in second sliding core member 3. Bladder 4 is affixed to support core 32 at two positions 8a and 8b that are selected based on the desired fill volume of the bladder. First sliding core member 1 and second sliding core member 3 are longitudinally extendible relative to each other along an axis 8 of pump 30. The extension of the sliding core members 1 and 3 guides the longitudinal and concentric extension of bladder 4 into an elliptical shape. This relative motion of sliding core members 1 and 3 causes a relative displacement of positions 8a and 8b, which are separated by a variable distance 8c. While fluids are being introduced into bladder 4, the distance 8c increases as bladder 4 expands and support core 32 elongates. While fluid is being delivered from bladder 4, the distance 8c decreases as bladder 4 contracts and support core 32 retracts. FIG. 2A shows support core 32 in its start position with little fluid in bladder 4. Referring to FIG. 2B, as fluids are introduced into bladder 4 and sliding core member 1 extends longitudinally relative to sliding core member 3, bladder 4 expands into a balloon-like shape.

Figure 4A:
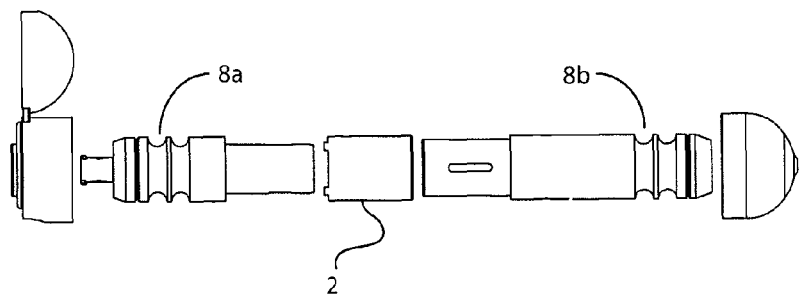
FIG. 4A is an expanded side view of a portion of a sliding core pump.
Figure 4B:
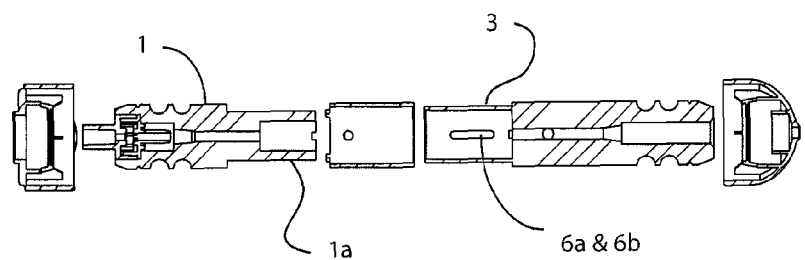
FIG. 4B is an expanded top cross-sectional view of a portion of a sliding core pump.

The relative longitudinal movement of sliding core members 1 and 3 along axis 8 is limited by ball bearings 5, which are typically made of glass or a medical grade polymer. Ball bearings 5 are located in slots 6 and/or channels or grooves 7 in sliding core members 1 and 3. The limit of the extension of support core 32 is determined by the length of slots 6 and channels 7. In the embodiment shown in FIGS. 4A and 4B, two slots 6a and 6b and two channels 7a and 7b are utilized. In general, the number of ball bearings 5, slots 6, and channels 7 varies depending on the size of support core 32 and the desired relative displacement between positions 8a and 8b. In other embodiments, the longitudinal movement of sliding core members 1 and 3 is limited by a stopper and guide assembly or by any other design that permits free movement of sliding core members 1 and 3 along axis 8 while also providing predetermined end points or limits to this movement.

Bladder 4 is formed of a flexible membrane that enables air trapped within the bladder to slowly dissipate through the permeable membrane. In some embodiments, bladder 4 is made of a self-venting material. The material of bladder 4 is also compatible with pharmaceutical compounds. For instance, bladder 4 is made of silicone or another rubber polymer. In some embodiments, bladder 4 is made primarily of silicone.

Referring again to FIG. 2B, cover 34 protects bladder 4 (e.g., from puncture, abrasion, or dirt) and provides a surface area for printing variable manufacturing data and device identification, such as lot numbers, fill volume, flow rates, and flow duration. Cover 34 is formed to enclose bladder 4 in both its filled state and its unfilled state without deforming or otherwise affecting the general shape or position of the bladder relative to support core 32 as bladder 4 expands and contracts. That is, as bladder 4 is filled with fluid, the bladder takes on a shape and position that is independent of the size and shape of cover 34. In one example, cover 34 is vacuum formed to have an air gap 35 between an inner surface 38 of the cover and an outer surface 36 of bladder 4 in its fully filled state. Cover 34 is secured (for example, with elastic bands, not shown) to support core 32 at positions 40a and 40b. Because cover 34 is affixed to support core 32 and moves in tandem with sliding core members 1 and 3, the ends of cover 34 extend longitudinally away from each other as bladder 4 expands. Cover 34 may be a soft cover that is made, for instance, of PVC. In other examples, a hard rigid cover protects bladder 4. The hard rigid cover may fully or partially enclose bladder 4 in its fully-expanded state without deforming or otherwise affecting the general shape or position of the bladder relative to support core 32 as bladder 4 expands and contracts.

Figure 4C:
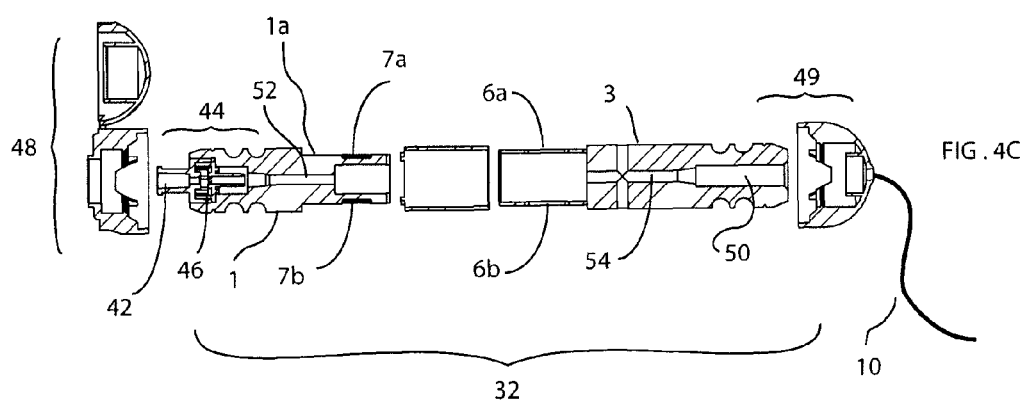
FIG. 4C is an expanded side cross-sectional view of a portion of a sliding core pump.

Referring to FIG. 4C, pump 30 includes a filling port 42 at an open end 44 of support core 32 through which fluids are introduced into bladder 4. Filling port 42 is compatible with most syringes and other standard filling devices. A one-way anti-siphon valve 46 on filling port 42 prevents leakage of fluid from bladder 4 during and after filling. A flip cap assembly 48 is attached to support core 32 to cover filling port 42. At an opposite end 49 of support core 32, an output port 50 is connected to fluid delivery line 10. Two flow paths 52 and 54 extend within support core 32. Flow path 52 couples filling port 42 with the inside of bladder 4, while flow path 54 couples the inside of bladder 4 with output port 50.

Figure 1:
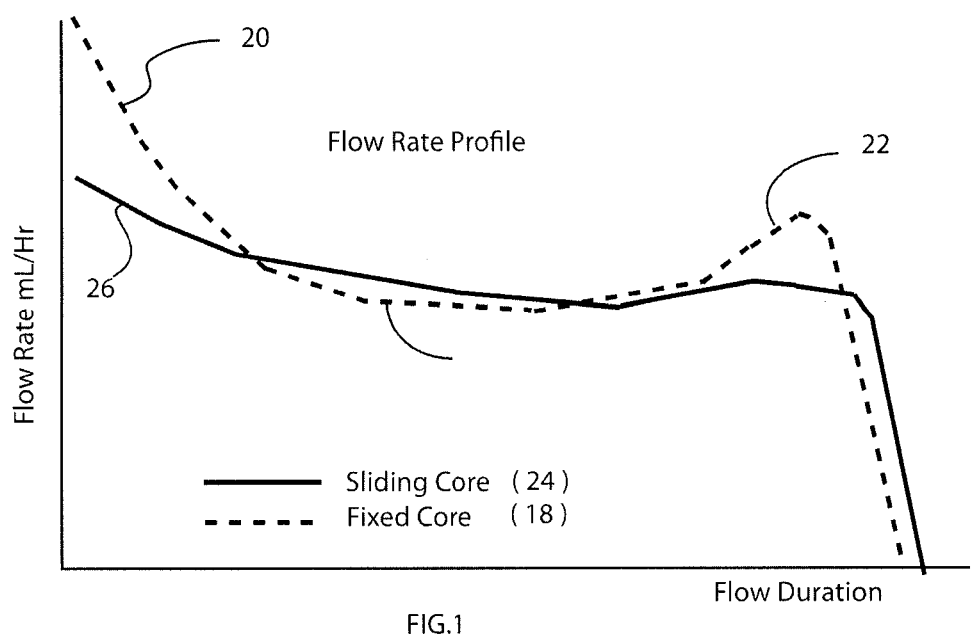
FIG. 1 shows flow rate profiles for a standard elastomeric pump and a sliding core pump.

The construction of support core 32 to including sliding core members 1 and 3 imparts an additional degree of movement to pump 30 as the bladder is filled or as fluid is delivered from the pump. Referring again to FIG. 1, this additional degree of movement gives a flow profile 24 to sliding core pump 30. As fluid is initially delivered from the pump, bladder 4 contracts and sliding core members 1 and 3 move longitudinally inwards. The motion of sliding core members 1 and 3 allows bladder 4 to exert less pressure on the fluid contained therein. The reduced force causes a minimal initial spike 26 at the beginning of fluid delivery.

Once sliding core members 1 and 3 have retreated to their home position (i.e., when sliding core members 1 and 3 are in contact or when distance 8c is at a minimum), bladder 4 continues to contract and expel fluid but there is no further retraction of support core 32. At this point, the flow rate enters a phase 28 that is comparable to the flow rate obtained during delivery from a pump without a sliding core. By adjusting the distance 8c in relation to the dimensions, wall thickness, geometry, and elasticity of bladder 4, an approximately flat flow rate profile can be achieved for sliding core pump 30.

In some embodiments, various modes of fluid delivery are available, including continuous flow, continuous flow with Bolus effect, Bolus flow, and variable flow.

The foregoing description is intended to illustrate and not to limit the scope of the invention, which is defined by the scope of the appended claims. These and other embodiments are within the scope of the following claims.

What is claimed is:

1. A pump for delivery of a fluid, comprising:
   a support core including a first sliding core member and a second sliding core member configured to move relative to each other to longitudinally extend the support core along an axis of the pump;
   an expandable bladder, having an inside, the expandable bladder attached to the support core in at least one position and configured to receive a fluid;
   a filling port coupled to the first sliding core member and an output port coupled to the second sliding core member, the first sliding core member including a first flow path extending from the filling port to the inside of the expandable bladder and the second sliding core member including a second flow path extending from the inside of the expandable bladder to the output port, wherein the first flow path and the second flow path are separate and distinct from one another; and
   a restrictor configured to limit the longitudinal extension of the support core to a predetermined maximum length.

2. The pump of claim 1, further comprising a cover enclosing the bladder and at least a portion of the support core.

3. The pump of claim 2, wherein the cover has a size and shape such that when the bladder is filled with a fluid, the bladder has a size and position that are substantially independent of the size and shape of the cover.

4. The pump of claim 2, wherein the cover is sized and dimensioned such that a gap exists between an outer surface of the bladder and an inner surface of the cover when the bladder is filled with fluid.

5. The pump of claim 1, wherein the bladder is formed substantially of silicone.

6. The pump of claim 1, wherein the position at which the bladder is attached to the support core is selected based on at least one of a volume of the bladder when filled with fluid and a desired flow rate of a fluid delivered from the pump.

7. The pump of claim 1, wherein the first sliding core member and the second sliding core member are configured to slide longitudinally relative to each other.)

8. The pump of claim 7, further comprising a connector for connecting the first sliding core member and the second sliding core member.

9. The pump of claim 1, wherein the restrictor comprises a ball bearing positioned in a channel.

10. The pump of claim 9, wherein the length of the channel is determined based on the predetermined maximum length of the support core.

11. The pump of claim 1, wherein the support core is configured to expand longitudinally when fluid enters the bladder and to contract longitudinally when fluid exits the bladder.

12. The pump of claim 1, wherein the pump is configured to deliver fluid at a substantially constant flow rate.

13. A method for the delivery of a fluid from a pump, comprising:
   receiving fluid into a bladder through a filling port, including
      extending a support core including a first sliding core member and a second sliding core member configured to move relative to each other longitudinally to extend the support core along an axis of the pump, the first sliding core member coupled to the filling port and the second sliding core member coupled to the output port, the first sliding core member including a first flow path extending from the filling port to the inside of the expandable bladder and the second sliding core member including a second flow path extending from the inside of the expandable bladder to the output port,
   wherein the first flow path and the second flow path are separate and distinct from one another, and
      expanding the bladder,
         the extension of the support core limited to a predetermined maximum length by a restrictor; and
   delivering fluid from the pump through the output port, including
      contracting the bladder, and
      retracting the support core along the longitudinal axis of the pump.

14. The method of claim 13, wherein delivering fluid from the pump includes delivering fluid at a substantially constant flow rate.

15. The method of claim 13, wherein extending the support core includes sliding the first sliding core member of the support core longitudinally relative to the second sliding core member of the support core.

16. The method of claim 13, wherein expanding the bladder includes expanding the bladder to a shape and position that is substantially independent of a size and shape of a cover enclosing the bladder.

17. The method of claim 13, wherein the bladder is formed substantially of silicone.

* * * * *